(12) United States Patent
Rao et al.

(10) Patent No.: US 6,194,619 B1
(45) Date of Patent: Feb. 27, 2001

(54) GEM-DIHYDROPOLYFLUOROALKANES AND MONOHYDROPOLYFLUOROALKENES, PROCESSES FOR THEIR PRODUCTION, AND USE OF GEM-DIHYDROPOLYFLUOROALKANES IN CLEANING COMPOSITIONS

(75) Inventors: V. N. Mallikarjuna Rao; Frank Julian Weigert; Carl G. Krespan, all of Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 08/116,938

(22) Filed: Sep. 10, 1993

Related U.S. Application Data

(62) Division of application No. 07/751,019, filed on Aug. 28, 1991, now Pat. No. 5,268,122.

(51) Int. Cl.$^7$ .................................................. C07C 19/08
(52) U.S. Cl. ......................................... 570/124; 570/134
(58) Field of Search ................................. 570/134, 124

(56) References Cited

U.S. PATENT DOCUMENTS

| | | |
|---|---|---|
| 2,917,559 | 12/1959 | Sweeney et al. . |
| 2,975,220 | 3/1961 | Hauptschein et al. . |
| 2,999,815 | 9/1961 | Eiseman . |
| 2,999,817 | 9/1961 | Bower . |
| 3,449,304 | 6/1969 | Harris ................ 260/80.76 |
| 3,520,786 | 7/1970 | Rifi . |
| 3,573,213 | 3/1971 | Burt . |
| 3,728,268 | 4/1973 | Burt . |
| 3,789,006 | 1/1974 | McMillan et al. . |
| 3,881,949 | 5/1975 | Brock . |
| 3,903,009 | 9/1975 | Bauer et al. . |
| 4,418,185 | 11/1983 | Thruckmorton et al. . |
| 4,440,971 | 4/1984 | Harrold . |
| 4,715,900 | 12/1987 | Connon et al. . |
| 4,820,883 | 4/1989 | Weigert . |
| 4,820,884 | 4/1989 | Weigert . |
| 4,902,838 | 2/1990 | Manzer . |
| 4,947,881 | 8/1990 | Magid et al. . |
| 5,059,728 | 10/1991 | Li et al. . |
| 5,064,559 | 11/1991 | Merchant et al. .............. 252/171 |
| 5,064,560 | 11/1991 | Merchant . |
| 5,100,572 | 3/1992 | Merchant . |
| 5,162,594 | 11/1992 | Krespan . |
| 5,171,902 | 12/1992 | Krespan et al. . |

FOREIGN PATENT DOCUMENTS

| | | |
|---|---|---|
| 365 296 | 10/1989 | (EP) . |
| 376 686 | 7/1990 | (EP) . |
| 431 458 | 6/1991 | (EP) . |
| 458 279 | 11/1991 | (EP) . |

OTHER PUBLICATIONS

Morrison and Boyd, "Organic Chemistry", 3rd edition (Chinese version), pp. 131, 165 and 167. (See IDS), 1991.
C. Zhanxun et al., Adv. Low–Temp. Plasma Chem., *Technol. Appl.* (1988).
C. Zhanxun et al., Proc. Annual. Int. Conf. Plasma Chem., *Technol., Appl.* (1989).
R. D. Chambers et al., *Tetra.* pp. 4217–4234 (1969).
R. J. Hertzman et al., *J. Chem. Soc.* pp. 281–289 (1963).
V. A. Petrov et al., *Bull. Acad. Sci. USSR Div. Chem. Sci.*, 31(7):1414–1416 (Jan. 20, 1983).
R. Sullivan et al., *J. Org. Chem.* 29:3664–3668 (1964).
R. E. Banks et al., *J. Organomet. Chem.* 29:427–431 (1971).
V. V. Bardin et al., *J. Fluor. Chem.* 49:385–400 (1990).
A. E. Pedler et al., *J. Fluor. Chem.* pp. 337–345 (1971/72).

*Primary Examiner*—Alan Siegel

(57) ABSTRACT

A catalyic process is disclosed for producing fluorine-substituted hydrocarbon products of the formulae $RCH_2CF_2R$ and $RFC=CHR$ at an elevated temperature, from compounds of the formula $RCHFCHFR$, where each R is independently selected from the group consisting of $—CF_3$, $—CF_2CF_3$ and $—CF_2CF_2CF_3$ or where both R groups of a formula together are $—(CF_2)_2—$, $—(CF_2)_3—$ or $—(CF_2)_4—$. Suitable catalysts include carbon catalysts and catalysts containing at least one compound of a selected metal (e.g., Na, K, Rb, Cs, Y, La, Ce, Pr, Nd, Sm, Cr, Fe, Co, Rh, Ni, Cu, and/or Zn) supported on carbon.

The saturated gem-dihydro- products may also be produced by hydrofluorinating the corresponding olefinic product over such catalysts at an elevated temperature, and can be combined with various other miscible solvents to form compositions useful for cleaning. Compounds such as $CF_3CF_2CH_2CF_2CF_3$, $CF_3CF_2CH_2(CF_2)_2CF_3$, $CF_3CH=CF(CF_2)_2CF_3$, $CF_3CF=CH(CF_2)_2CF_3$, $CF_3CF_2CH_2(CF_2)_3CF_3$, $CF_3(CF_2)_2CH_2(CF_2)_2CF_3$, $CF_3CH=CF(CF_2)_3CF_3$, $CF_3CF=CH(CF_2)_3CF_3$, $CF_3(CF_2)_2CH_2(CF_2)_3CF_3$, $CF_3CF_2CH_2(CF_2)_4CF_3$, $CF_3CH=CF(CF_2)_4CF_3$, $CF_3CF=CH(CF_2)_4CF_3$, $CF_3CF_2CH=CF(CF_2)_3CF_3$, $CF_3CF_2CF=CH(CF_2)_3CF_3$ and

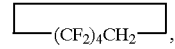

and azeotropic compositions such as azeotropes of $CF_3CH_2CF_2CF_2CF_3$ and/or $CF_3CF_2CH_2CF_2CF_3$ with methanol, ethanol, or isopropanol are disclosed.

8 Claims, No Drawings

US 6,194,619 B1

GEM-DIHYDROPOLYFLUOROALKANES AND MONOHYDROPOLYFLUOROALKENES, PROCESSES FOR THEIR PRODUCTION, AND USE OF GEM-DIHYDROPOLYFLUOROALKANES IN CLEANING COMPOSITIONS

This is a division of application Ser. No. 07/751,019, filed Aug. 28, 1991, now U.S. Pat. No. 5,268,122.

FIELD OF THE INVENTION

This invention relates to fluorine-substituted hydrocarbon compounds, their production, and their use for cleaning solid surfaces, and more particularly to polyfluorooctanes, polyfluorooctenes, polyfluoroheptanes, polyfluoroheptenes, and linear and cyclic polyfluorohexanes, polyfluorohexenes, polyfluoropentanes, polyfluoropentenes, polyfluorobutanes, and polyfluorobutenes, their production from linear and cyclic polyfluoroalkane or polyfluoroolefin starting materials, and the use of linear and cyclic polyfluoroalkanes as solvents.

BACKGROUND OF THE INVENTION

Various organic solvents have been used as cleaning liquids for the removal of contaminants from contaminated articles and materials. Certain fluorine-containing organic compounds such as 1,1,2-trichloro-1,2,2-trifluoroethane have been reported as useful for this purpose, particularly with regard to cleaning organic polymers and plastics which may be sensitive to other more common and more powerful solvents such as trichloroethylene or perchloroethylene. Recently, however, there have been efforts to reduce the use of certain compounds such as trichlorotrifluoroethane which also contain chlorine because of a concern over their potential to deplete ozone, and to thereby affect the layer of ozone that is considered important in protecting the earth's surface from ultraviolet radiation.

Boiling point, flammability and solvent power can often be adjusted by preparing mixtures of solvents. For example, certain mixtures of 1,1,2, -trichloro-1,2,2-trifluoroethane with other solvents (e.g., isopropanol and nitromethane) have been reported as useful in removing contaminants which are not removed by 1,1,2-trichloro-1,2,2-trichloroethane alone, and in cleaning articles such as electronic circuit boards where the requirements for a cleaning solvent are relatively stringent, i.e., it is generally desirable in circuit board cleaning to use solvents which have low boiling points, are non-flammable, have low toxicity, and have high solvent power so that flux such as rosin and flux residues which result from soldering electronic components to the circuit board can be removed without damage to the circuit board substrate).

While boiling point, flammability, and solvent power can often be adjusted by preparing mixtures of solvents, the utility of the resulting mixtures can be limited for certain applications because the mixtures fractionate to an undesirable degree during use. Mixtures can also fractionate during recovery, making it more difficult to recover a solvent mixture with the original composition. Azeotropic compositions, with their constant boiling and constant composition characteristics, are thus considered particularly useful.

Azeotropic compositions exhibit either a maximum or minimum boiling point and do not fractionate upon boiling. These characteristics are also important in the use of the solvent compositions in certain cleaning operations, such as removing solder fluxes and flux residues from printed circuit boards. Preferential evaporation of the more volatile components of the solvent mixtures, which would be the case if the mixtures were not azeotropes, or azeotrope-like, would result in mixtures with changed compositions which may have less desirable properties (e.g., lower solvency for contaminants such as rosin fluxes and/or less inertness toward the substrates such as electrical components).

Azeotropic characteristics are also desirable in vapor degreasing operations where redistilled material is usually used for final rinse-cleaning. Thus, the vapor defluxing or degreasing system acts as a still. Unless the solvent composition exhibits a constant boiling point (i.e., is an azeotrope or is azeotrope-like) fractionation will occur and undesirable solvent distribution may act to upset the safety and effectiveness of the cleaning operation.

A number of azeotropic compositions based upon halohydrocarbons containing fluorine have been discovered and in some cases used as solvents for the removal of solder fluxes and flux residues from printed circuit boards and for miscellaneous vapor degreasing applications. For example, U.S. Pat. No. 2,999,815 discloses the azeotrope of 1,1,2-trichloro-1,2,2-trifluoroethane with acetone; U.S. Pat. No. 3,903,009 discloses a ternary azeotrope of 1,1,2-trichloro-1,2,2-triflouroethane with nitromethane and ethanol; U.S. Pat. No. 3,573,213 discloses an azeotrope of 1,1,2-trichloro-1,2,2-trifluoroethane with nitromethane; U.S. Pat. No. 3,789,006 discloses the ternary azeotrope of 1,1,2-trichloro-1,2,2-trifluoroethane with nitromethane and isopropanol; U.S. Pat. No. 3,728,268 discloses the ternary azeotrope of 1,1,2-trichloro-1,2,2-trifluoroethane with acetone and ethanol; U.S. Pat. No. 2,999,817 discloses the binary azeotrope of 1,1,2-trichloro-1,2,2-trifluoroethane and methylene chloride (i.e., dichloromethane); and U.S. Pat. No. 4,715,900 discloses ternary compositions of trichlorotrifluoroethane, dichlorodifluoroethane, and ethanol or methanol.

As noted above, many solvent compositions which have proven useful for cleaning contain at least one component which is a halogen-substituted hydrocarbon containing chlorine, and there have been concerns raised over the ozone depletion potential of halogen-substituted hydrocarbons which contain chlorine. Efforts are being made to develop compositions which may at least partially replace the chlorine containing components with other components having lower potential for ozone depletion. Azeotropic compositions of this type are of particular interest.

Means of synthesizing various fluorine-substituted alkanes have been reported.

U.S. Pat. No. 2,917,559 discloses a vapor phase process for the production of 2-fluoropropane by the reaction of HF and propylene over an activated carbon catalyst.

U.S. Pat. No. 2,975,220 discloses compounds of the general formula $R(CH_2CF_2)nQ$, where n is an integer and Q is halogen or hydrogen and R is a halogenated radical. These compounds (e.g., $CF_3CH_2CF_2CF_2CF_3$) may be prepared by reacting vinylidene fluoride with certain telogens.

U.S. Pat. No. 3,520,786 discloses a process for the preparation of cycloalkanes by electrolyzing a solution of halocarbons having 3–6 ring carbons of the general composition $C(R_1)RR—C(_{1-4})RR—C(R_2)RR$, where R may be an alkyl group, hydrogen, or a halogen; $R_1$ is halogen; and $R_2$ may be a halogen, quarternary ammonium salt or a tosylate; and isolating the corresponding cycloalkane.

U.S. Pat. No. 4,902,838 discloses a process for the isomerization of $C_2$ to $C_6$ hydrofluorocarbons having lesser thermodynamic stability to hydrofluorocarbons having greater thermodynamic stability by isomerization in the vapor phase of at least one $C_2$ to $C_6$ saturated hydrofluorocarbon with a catalyst comprising aluminum fluoride. The isomerization of 1,1,2,2-tetrafluoroethane, a vicinal-dihydro fluorocarbon, to 1,1,1,2-tetrafluoroethane, a geminal-dihydro fluorocarbon, is exemplified.

Eur. Pat. Appln. No. 365,296 discloses a process for the preparation of 1,1,1,2-tetrafluoroethane by the isomerization of 1,1,2,2-tetrafluoroethane over a fluorination catalyst. The only catalyst exemplified is chromia.

C. Zhanxun et al., Proc. Annu. Int. Conf. Plasma Chem. Technol., 4th, Meeting Date 1987, 173-9 (1989) and C. Zhanxun et al., Adv. Low-Temp. Plasma Chem., Technol., Appl., 2, 265-73 (1988) discloses the formula $CF_3CF_2CH_2CF_2CF_3$ as a theoretical product from the degradation of plasma-polymerized tetrafluoroethylene.

There are also means of synthesizing various fluorine-substituted alkenes. For example, U.S. Pat. Nos. 4,820,883 and 4,820,884 disclose the use of activated carbon for the preparation of unsaturated fluorocarbons by defluorinating perfluoro compounds.

SUMMARY OF THE INVENTION

In accordance with this invention, novel saturated compounds are provided which contain no chlorine and which may be used alone or in combination with various other miscible solvents as agents for cleaning solid surfaces. Novel unsaturated compounds, which may be used for preparation of the corresponding saturated compounds, are also provided in accordance with this invention.

The novel compounds of this invention include the group of dihydropolyfluoropentanes, dihydropolyfluorohexanes, dihydropolyfluoroheptanes and dihydropolyfluorooctanes represented by the formula $R^1CH_2CF_2R^2$ wherein $R^1$ is selected from the group consisting of $—CF_2CF_3$ and $—CF_2CF_2CF_3$ and $R^2$ is selected from the group consisting of $—CF_3$, $—CF_2CF_3$ and $—CF_2CF_2CF_3$ or wherein $R^1$ and $R^2$ together are $—(CF_2)_3—$; and the group of monohydropolyfluoroolefins represented by the formula $R^3X^1C=CX^2R^4$ wherein $R^3$ is selected from the group consisting of $—CF_3$ and $—CF_2CF_3$, $R^4$ is selected from the group consisting of $—CF_2CF_2CF_3$, $—CF_2CF_2CF_2CF_3$ and $—CF_2CF_2CF_2CF_2CF_3$, and $X^1$ and $X^2$ are different and are selected from the group consisting of hydrogen and fluorine, provided that when $R^3$ is $—CF_2CF_3$ $R^4$ is $—CF_2CF_2CF_2CF_3$.

A process is provided in accordance with this invention for preparing compounds selected from the group consisting of gem-dihydropolyfluoroalkanes of the formulae $R^5CH_2R^6$ and $R^5CF_2CH_2R^6$ and monohydropolyfluoroolefins of the formulae $R^5CH=CFR^6$ and $R^5CF=CHR^6$ wherein $R^5$ and $R^6$ are each independently selected from the group consisting of $—CF_3$, $—CF_2CF_3$ and $—CF_2CF_2CF_3$, or wherein $R^5$ and $R^6$ together are $—(CF_2)_2—$, $—(CF_2)_3—$ or $—(CF_2)_4—$, which comprises the step of contacting a saturated starting material of the formula $R^5CHFCHFR^6$ wherein $R^5$ and $R^6$ are as above, at an elevated temperature with a carbon catalyst or a catalyst containing at least one compound of a metal selected from the group consisting of sodium, potassium, rubidium, cesium, yttrium, lanthanum, cerium praseodymium, neodymium, samarium, chromium, iron, cobalt, rhodium, nickel, copper, zinc, and mixtures thereof, supported on carbon.

Another process is provided in accordance with this invention for preparing gem-dihydropolyfluoroalkanes of the formula $R^7CH_2CF_2R^8$ wherein $R^7$ and $R^8$ are each independently selected from the group consisting of $—CF_3$, $—CF_2CF_3$ and $—CF_2CF_2CF_3$ or wherein $R^7$ and $R^8$ together are $—(CF_2)_2—$, $—(CF_2)_3$ or $—(CF_2)_4—$, which comprises the step of reacting an olefinic starting material of the formula $R^7CH=CFR^8$ wherein $R^7$ and $R^8$ are as above, with HF at an elevated temperature in the presence of a carbon catalyst or a catalyst of at least one compound of a metal selected from the group consisting of sodium, potassium, rubidium, cesium, yttrium, lanthanum, cerium praseodymium, neodymium, samarium, chromium, iron, cobalt, rhodium, nickel, copper, zinc, and mixtures thereof, supported on carbon. The gem-dihydropolyfluoroalkanes may be used in combination with other miscible solvents (e.g., alcohols, ethers, esters, ketones, nitrogen-containing organic compounds such as acetonitrile and nitromethane, and halogenated hydrocarbons) as agents for cleaning solid surfaces.

DETAILED DESCRIPTION OF THE INVENTION

This invention provides novel saturated linear polyfluorohydrocarbons which contain two hydrogen atoms per molecule which are attached to the same carbon atom (i.e., gem-dihydropolyfluoroalkanes). The novel gem-dihydropolyfluoroalkanes of this invention have the formula $R^1CH_2CF_2R^2$ wherein $R^1$ is selected from the group consisting of $—CF_2CF_3$ and $—CF_2CF_2CF_3$ and $R^2$ is selected from the group consisting of $—CF_3$, $—CF_2CF_3$ and $—CF_2CF_2CF_3$ or wherein $R^1$ and $R^2$ together are $—(CF_2)_3—$, and include the dihydropolyfluorooctanes $CF_3CF_2CH_2CF_2CF_2CF_2CF_2CF_3$ and $CF_3CF_2CF_2CH_2CF_2CF_2CF_2CF_3$; the dihydropolyfluoroheptanes $CF_3CF_2CH_2CF_2CF_2CF_2CF_3$ and $CF_3CF_2CF_2CH_2CF_2CF_2CF_3$; the dihydropolyfluorohexane $CF_3CF_2CH_2CF_2CF_2CF_3$; the dihydropolyfluoropentane $CF_3CF_2CH_2CF_2CF_3$; and the compound

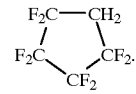

This invention also provides novel polyfluoroolefins which contain one hydrogen atom per molecule which is attached to one of the carbons forming the olefinic bond. The novel monohydropolyfluoroolefines of this invention have the formula $R^3X^1C=CX^2R^4$ wherein $R^3$ is selected from the group consisting of $—CF_3$ and $—CF_2CF_3$, $R^4$ is selected from the group consisting of $—CF_2CF_2CF_3$, $—CF_2CF_2CF_2CF_3$ and $—CF_2CF_2CF_2CF_2CF_3$, and $X^1$ and $X^2$ are different and are selected from the group consisting of hydrogen and fluorine, provided that when $R^3$ is $—CF_2CF_3$ $R^4$ is $—CF_2CF_2CF_2CF_3$, and include the monohydropolyfluorohexenes $CF_3CH=CFCF_2CF_2CF_3$ and $CF_3CF=CHCF_2CF_2CF_3$; the monohydropolyfluoroheptanes $CF_3CH=CFCF_2CF_2CF_2CF_3$ and $CF_3CF=CHCF_2CF_2CF_2CF_3$; and the monohydropolyfluorooctenes $CF_3CH=CFCF_2CF_2CF_2CF_2CF_3$, $CF_3CF=CHCF_2CF_2CF_2CF_2CF_3$, $CF_3CF_2CH=CFCF_2CF_2CF_2CF_3$ and $CF_3CF_2CF=CHCF_2CF_2CF_2CF_3$.

A process provided in accordance with this invention for preparing compounds selected from the group consisting of gem-dihydropolyfluoroalkanes of the formula $R^5CH_2CF_2R^6$ and $R^5CF_2CH_2R^6$ and monohydropolyfluoroolefins of the formulae $R^5CH=CFR^6$ and $R^5CF=CHR^6$ wherein $R^5$ and $R^6$ are each selected from the group consisting of —$CF_3$, —$CF_2CF_3$ and —$CF_2CF_2CF_3$ or wherein $R^5$ and $R^6$ together are —$(CF_2)_2$—, —$(CF_2)_3$— or —$(CF_2)_4$—, comprises the step of contacting a saturated starting material of the formula $R^5CHFCHFR^6$, wherein $R^5$ and $R^6$ are as above, at an elevated temperature with a carbon catalyst or a catalyst of at least one compound of a metal selected from the group consisting of sodium, potassium, rubidium, cesium, yttrium, lanthanum, cerium praseodymium, neodymium, samarium, chromium, iron, cobalt, rhodium, nickel, copper, zinc, and mixtures thereof, supported on carbon. The carbon which is used as a catalyst can be either unwashed or acid washed. The washed carbon is normally prepared by treating the carbon with acid containing neither phosphorus nor sulfur, to remove impurities. Preferably a subsequent treatment is done with hydrofluoric acid to further reduce impurities, especially silicon. After such treatment the ashed carbon typically contains less than about 0.1% ash. Commercially available carbons useful in the process of this invention include those sold under the following trademarks: Darco™, Nuchar™, Columbia SBV™, MBV™, Columbia MBQ™, Columbia JXC™, Columbia CXC™, Calgon PCB™, and Barnaby Cheny NB™. The carbon catalyst can be in the form of powder, granules, or pellets, etc. High surface area carbons such as Calgon® PCB and Carbosieve G® are preferred over low surface area carbons. Examples of acids which may be used in the first acid wash of this process include organic acids such as acetic acid and inorganic acids, e.g., HCl or $HNO_3$. Preferably hydrochloric acid or nitric acid is used. The acid treatment may be accomplished in several ways. A preferred embodiment is described below.

A carbon catalyst is soaked overnight with gentle stirring in a 1M solution of the acid prepared in deionized water. The carbon catalyst is separated and washed with deionized water until the pH of the washings is about 3. The carbon catalyst is then soaked again, with gentle stirring in a 1M solution of the acid prepared in deionized water, for about 12 to 24 hours. The carbon catalyst is then finally washed with deionized water until the washings are substantially free of the anion of the acid (e.g., cl⁻ or $NO_3^-$), when tested by standard procedures. The carbon catalyst is then separated and dried at about 120°C. a sample of this washed carbon is the soaked, if desired, in 1 M HF prepared in deionized water for about 48 hours at room temperature with occasional stirring in an HF-resistant container. The carbon catalyst is separated and washed repeatedly with deionized water until the pH of the washings is greater than 4. The carbon catalyst is then dried at about 150° C., followed by calcination at about 300° C. Suitable carbons include acid washed carbons (e.g., carbons essentially free of K⁻) or unwashed carbons (e.g., carbons containing from about 0.1 to about 2 percent by weight K⁻). Metal compounds supported on carbon may also be used for either the rearrangement of vicinal-dehydropolyfluoroalkanes to geminal-dihydropolyfluoroalkanes or the dehydro-fluorination of vicinal-dihydropolyfluoroalkanes to mixtures of monohydropolyfluoroolefins. The metals of the compounds may be selected from the group consisting of sodium, potassium, rubidium, cesium, yttrium, the lanthanide series especially, lanthanum, cerium, praseodymium, neodymium, and samarium, chromium, iron, cobalt, rhodium, nickel, copper, zinc, and mixtures thereof. Example compounds include the acetates, nitrates, chlorides and/or fluorides of said metals. The carbon supported metal compounds may be prepared from soluble metal salts by known art procedures. Generally, where carbon-supported metal compounds are used, the metals comprise from about 0.5 to 30 percent by weight of the catalyst.

HF may be added during the isomerization. Through catalyst selection and process control, as described herein, the ratio of monohydropolyfluoro-olefins to geminal-dihydropolyfluoroalkanes can be adjusted. For example, higher pressures favor the formation of geminal-dihydropolyfluoroalkanes. Alternatively, the proportion of monohydropolyfluoroolefins may be increased by adding inert gases such as nitrogen, helium or argon to the reactor feed.

Unreacted starting materials and intermediates, if any, may be separated from the reaction products by conventional means (e.g., distillation) and recycled back into the reactor.

The saturated starting material used for this process has the same number of carbon atoms as the desired gem-dihydropolyfluoroalkane and/or monohydropolyfluoroolefin. Thus, the gem-dihydropolyfluoroalkane $CF_3CH_2CF_2CF_3$ can be produced by isomerizing $CF_3CFHCFHCF_3$ over a carbon-containing catalyst in accordance with this invention; a gem-dihydropolyfluoroalkane selected from the group consisting of $CF_3CH_2CF_2CF_2CF_3$ and $CF_3CF_2CH_2CF_2CF_3$ can be produced by isomerizing $CF_3CHFCHFCF_2CF_3$ over a carbon-containing catalyst in accordance with this invention; a gem-dihydropolyfluoroalkane selected from the group consisting of $CF_3CH_2CF_2CF_2CF_2CF_3$ and $CF_3CF_2CH_2CF_2CF_2CF_3$ can be produced by isomerizing a $CF_3CHFCHFCF_2CF_2CF_3$ over a carbon-containing catalyst in accordance with this invention; the gem-dihydropolyfluoroalkane $CF_3\ CF_2CH_2CF_2CF_2CF_3$ can be produced by isomerizing $CF_3CF_2CHFCHFCF_2CF_3$ over a carbon-containing catalyst in accordance with this invention; a gem-dihydropoly-fluoroalkane selected from the group consisting of $CF_3CF_2CH_2CF_2CF_2CF_2CF_3$ and $CF_3CF_2CHFCHFCF_2CF_2CF_3$ over a produced by isomerizing $CF_3CF_2CHFCHFCF_2CF_2CF_3$ over a carbon-containing catalyst in accordance with this invention; a gem-dihydropolyfluoroalkane selected from the group consisting of $CF_3CH_2CF_2CF_2CF_2CF_2\ CF_3$ and $CF_3CF_2CH_2CF_2CF_2CF_2CF_3$ can be produced by isomerizing $CF_3CHFCHFCF_2CF_2CF_2CF_3$ over a carbon-containing catalyst in accordance with this invention; the gem-dihydropolyfluoroalkane $CF_3CF_2CF_2CH_2CF_2CF_2CF_2CF_3$ can be produced by isomerizing $CF_3CF_2CF_2CHFCHFCF_2CF_2CF_3$ over a carbon-containing catalyst in accordance with this invention; a gem-dihydropolyfluoroalkane selected from the group consisting of $CF_3CH_2CF_2CF_2CF_2CF_2CF_2CF_3$ and $CF_3CF_2CH_2CF_2CF_2CF_2CF_2CF_3$ can be produced by isomerizing $CF_3CHFCHFCF_2CF_2CF_2CF_2CF_3$ over a carbon-containing catalyst in accordance with this invention; a gem-dihydropolyfluoroalkane selected from the group consisting of $CF_3CF_2CH_2CF_2CF_2CF_2CF_2CF_3$ and $CF_3CF_2CF_2CH_2CF_2CF_2CF_2CF_3$ can be produced by isomerizing $CF_3CF_2CHFCHFCF_2CF_2CF_2CF_3$ over a carbon-containing catalyst in accordance with this invention; the compound

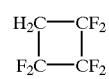

can be produced by isomerizing

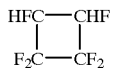

over a carbon-containing catalyst in accordance with this invention; the compound

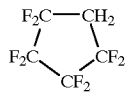

can be produced by isomerizing

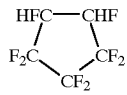

over a carbon-containing catalyst in accordance with this invention; and the compound

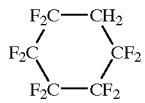

can be produced by isomerizing

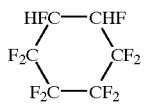

over a carbon-containing catalyst in accordance with this invention.

The monohydropolyfluoroolefin $CF_3CH=CFCF_3$ can be produced by dehydrofluorinating $CF_3CFHCFHCF_3$ over a carbon-containing catalyst in accordance with this invention; a monohydropolyfluoroolefin selected from the group consisting of $CF_3CH=CFCF_2CF_3$ and $CF_3CF=CHCF_2CF_3$ can be produced by dehydrofluorinating $CF_3CFHCFHCF_2CF_3$ over a carbon-containing catalyst in accordance with this invention; a monohydropolyfluoroolefin selected from the group consisting of $CF_3CH=CFCF_2CF_2CF_3$ and $CF_3CF=CHCF_2CF_2CF_3$ can be produced by dehydrofluorinating $CF_3CFHCFHCF_2CF_2CF_3$ over a carbon-containing catalyst in accordance with this invention; the monohydropolyfluoroolefin $CF_3CF_2CH=CFCF_2CF_3$ can be produced by dehydrofluorinating $CF_3CF_2CFHCFHCF_2CF_3$ over a carbon-containing catalyst in accordance with this invention; a monohydropolyfluoroolefin selected from the group consisting of $CF_3CF_2CH=CFCF_2CF_2CF_3$ and $CF_3CF_2CF=CHCF_2CF_2CF_3$ can be produced by dehydrofluorinating $CF_3CHFCHFCF_2CF_2CF_2CF_3$ over a carbon-containing catalyst in accordance with this invention; a monohydropolyfluoroolefin selected from the group consisting of $CF_3CH=CFCF_2CF_2CF_2CF_3$ and $CF_3CF=CHCF_2CF_2CF_2CF_3$ can be produced by dehydrofluorinating $CF_3CF_3CHFCHFCF_2CF_2CF_2CF_3$ over a carbon-containing catalyst in accordance with this invention; the monohydropolyfluoroolefin $CH_3CF_2CF_2CH=CFCF_2CF_2CF_3$ can be produced by dehydrofluorinating $CF_3CF_2CF_2CHFCHFCF_2CF_2CF_3$ over a carbon-containing catalyst in accordance with this invention; a monohydropolyfluoroolefin selected from the group consisting of $CF_3CH=CFCF_2CF_2CF_2CF_2$ $CF_3$ and $CF_3CF=CHCF_2CF_2CF_2CF_2CF_3$ can be produced by dehydrofluorinating $CF_3CHFCHFCF_2CF_2CF_2CF_2CF_3$ over a carbon-containing catalyst in accordance with this invention; a monohydropolyfluoroolefin selected from the group consisting of $CF_3CF_2CH=CFCF_2CF_2CF_2CF_3$ and $CF_3CF_2CF=CHCF_2CF_2CF_2CF_3$ can be produced by dehydrofluorinating $CF_3CF_2CHFCHFCF_2CF_2CF_2CF_3$ over a carbon-containing catalyst in accordance with this invention; the compound

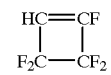

can be produced by dehydrofluorinating

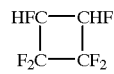

over a carbon-containing catalyst in accordance with this invention; the compound

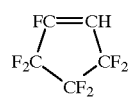

can be produced by dehydrofluorinating

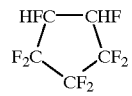

over a carbon-containing catalyst in accordance with this invention; and the compound

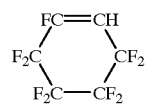

can be produced by dehydrofluorinating

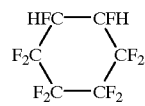

over a carbon-containing catalyst in accordance with this invention.

The isomerization and/or dehydrofluorinating can be carried out at temperatures in the range of from about 200° C. to about 500° C. The preferred temperature range is from about 300° C. to about 450° C. The pressure of the reaction may be within a wide range, from less than 1 atmosphere to extremely high pressures (e.g., 50 atmospheres or more), but normally pressures from 1 atmosphere to about 30 atmospheres are preferred, with higher pressures (e.g., 5 atmospheres or more) favoring the production of saturated products. The reaction time may also be within a wide range, depending upon such factors as the materials present, temperature and the conversion desired. Normally reaction times between about 15 seconds and 10 hr are suitable. If the olefinic products are desired, reaction times of about 30 seconds at about 1 atmosphere and temperatures within the range of about 250° C. to 350° C. are considered suitable in a continuous flow reactor. If the saturated products are desired, reaction times of about 150 seconds at about 7 atmospheres and temperatures within the range of about 250° C. to 350° C. are considered suitable in a continuous flow reactor.

Without limiting the invention to a particular theory of operation, it is believed that the saturated starting material may be sequentially converted during reaction to an olefinic material containing one hydrogen by removal of HF, and then hydrofluorinated back to a saturated end product wherein the hydrogen atoms are positioned on the same carbon.

Various saturated starting materials for this process may be prepared by hydrogenating olefinic perfluoroolefins of the type produced in U.S. patent application Ser. No. 07/595,839. The hydrogenation may be conducted in accordance with the procedures disclosed in U.S. patent application Ser. No. 07/595,840. U.S. patent application Ser. No. 07/595,839 and U.S. patent application Ser. No. 07/595,840 are hereby incorporated by reference in their entirety.

The vicinal linear dihydropolyfluoroalkane starting materials of this invention selected from the group consisting of $CF_3CHFCHFCF_3$, $CF_3CF_2CHFCHFCF_2CF_3$, $CF_3CHFCHFCF_2CF_2CF_3$, $CF_3CF_2CHFCHFCF_2CF_3$, $CF_3CHFCHFCF_2CF_2CF_2CF_3$, $CF_3CF_2CHFCHFCF_2CF_2CF_3$, $CF_3CHFCHFCF_2CF_2CF_2CF_2CF_3$, $CF_3CF_2CHFCHFCF_2CF_2CF_2CF_3$, and $CF_3CF_2CF_2CHFCHFCF_2CF_2CF_3$, may be prepared by a process which comprises reacting an appropriated olefinic starting material in the vapor phase with hydrogen over a Group VIII metal catalyst. Preferably the catalyst in a supported palladium. The appropriate olefinic starting material has the same number of carbon atoms as the desired vicinal linear dihydropolyfluoroalkane and is selected from the group consisting of $CF_3CF=CFCF_3$, $CF_3CF=CFCF_2CF_3$, $CF_3CF=CFCF_2CF_2CF_3$, $CF_3CF_2CF=CFCF_2CF_3$, $CF_3CF=CFCF_2CF_2CF_2CF_3$, $CF_3CF_2CF=CFCF_2CF_2CF_3$, $CF_3CF=CFCF_2CF_2CF_2CF_2CF_3$, $CF_3CF_2CF=CFCF_2CF_2CF_2CF_3$, and $CF_3CF_2CF_2CF=CFCF_2CF_2CF_3$; and has its olefinic bond between the carbon atoms which correspond to the hydrogen-bearing carbons in said dihydropolyfluoroalkanes. Unsupported metal catalysts and supported metal catalysts wherein the metal is palladium, rhodium or ruthenium are particularly suitable for use in this hydrogenation process. Supports such as carbon or alumina may be employed. Supported palladium catalysts are preferred.

The vapor phase reduction can be carried out in the range of from abut 50° C. to about 250° C.; the preferred temperature range is from about 100° C. to about 200° C. The pressure of the hydrogenation may vary widely from less than 1 atmosphere to 20 or more atmospheres. The molar ratio of hydrogen to olefinic starting material for this process is preferably between about 0.5:1 and 4:1, and is more preferably between about 0.5:1 and 1.5:1.

The vicinal dihydropolyfluorocycloalkane starting materials of this invention selected from the group consisting of 1H, 2H-perfluorocyclobutane, 1H,2H-perfluorocyclopentane, and 1H,2H-perfluorocyclohexane may be prepared by a process which comprises the step of reacting an olefinic starting material which has the same number of carbons as said dihydropolyfluorocycloalkane and is selected form the group consisting of perfluorocyclobutene, perfluorocyclopentene, and perfluorocyclohexane, at an elevated temperature with hydrogen in the presence of at least one material selected from the group consisting of iodine and hydrogen iodide (HI), or with hydrogen iodide. Iodine and /or HI is used for this hydrogenation in accordance with the teachings of U.S. patent application Ser. No. 07/607,754. Hydrogen iodide for the reaction may be provided by several methods. For example the reaction may be run with stoichiometric HI. Alternatively, the reaction may be run with catalytic amounts of HI in the presence of hydrogen. The reaction may also be run with hydrogen using catalytic amounts of iodine. The latter method is preferred for batch reactions and ease of handling. This reaction may be accomplished in the absence of supported metal catalysts; and indeed the catalyst for this reaction typically consists essentially of iodine and/or hydrogen iodide. The reaction temperature of this reaction should generally be from 100° C. to 500° C. A preferred temperature is from 200° C. to 400° C. This reaction may be run at a pressure of from about 50 psi to about 5000 psi, with 500 psi to 1500 psi being preferred.

The amount of hydrogen provided for contact with the olefinic starting material (either by addition of HI or by feed of hydrogen gas) should represent at least one molecule of hydrogen for each olefinic bond and is preferably no more than 10 times said minimum (i.e., the molar ration of hydrogen available for reacting to olefinic starting material is preferably between 10:1 and 1:1). When hydrogen gas is used, the hydrogen can be fed either in the pure state or diluted with an inert gas (e.g., nitrogen, helium or argon).

Another process provided in accordance with this invention for preparing gem-dihydropolyfluoroalkanes of the formula $R^7Ch_2CF_2R^8$ wherein $R^7$ and $R^8$ are each selected from the group consisting of $—CF_3$, $—CF_2CF_3$ and $—CF_2CF_2CF_3$ or wherein $R^7$ and $R^8$ together are $—(CF_2)_n—$ when n is an integer from 2 to 4, which comprises the step or reacting an olefinic starting material of the formula $R^7CH=CFR^8$ (Wherein $R^7$ and $R^8$ are as above) with HF at an elevated temperature in the presence of a carbon catalyst or a catalyst of at least one compound of a metal selected form the group consisting of sodium, potassium, rubidium, cesium, yttrium, lanthanum, cerium praseodymium, neodymium, samarium, chromium, iron, cobalt, rhodium, nickel, copper, zinc, and mixtures thereof, supported on carbon.

The olefinic starting material used for this process has the same number of carbon atoms as the desired gem-dihydropolyfluoroalkane. Thus, the gem-dihydropolyfluoroalkane $CF_3CH_2CF_2CF_3$ can be produced by reacting $CF_3CH=CFCF_3$ with HF over a carbon-containing catalyst in accordance with this invention; the gem-dihydropolyfluoroalkane $CF_3CH_2CF_2CF_2CF_3$ can be produced by reacting $CF_3CH=CFCF_2CF_3$ with HF over a carbon-containing catalyst in accordance with this invention; the gem-dihydropolyfluoroalkane $CF_3CF_2CH_2CF_2CF_3$ can be produced by reacting $CF_3CF_2CH=CFCF_3$ with HF over a carbon-containing catalyst in accordance with this invention; the gem-dihydropolyfluoroalkane $CF_3CH_2CF_2CF_2CF_2CF_3$ can be produced by reacting $CF_3CH=CFCF_2CF_2CF_3$ with HF over a carbon-containing catalyst in accordance with this invention; the gem-dihydropolyfluoroalkane $CF_3CF_2CH_2CF_2CF_2CF_3$ can be produced by reacting $CF_3CF_2CH=CFCF_2CF_3$ and/or $CF_3CF_2CF_2CH=CFCF_3$ with HF over a carbon-containing catalyst in accordance with this invention; the gem-dihydropolyfluoroalkane $CF_3CH_2CF_2CF_2CF_2CF_2CF_3$ can be produced by reacting $CF_3CH=CFCF_2CF_2CF_2CF_3$ with HF over a carbon-containing catalyst in accordance with this invention; the gem-dihydropolyfluoroalkane $CF_3CF_2CH_2CF_2CF_2CF_2CF_3$ can be produced by reacting $CF_3CF_2CH=CFCF_2CF_2CF_3$ and/or $CF_3CF=CHCF_2CF_2CF_2CF_3$ with HF over a carbon-containing catalyst in accordance with this invention; the gem-dihydropolyfluoroalkane $CF_3CF_2CF_2CH_2CF_2CF_2 CF_3$ can be produced by reacting $CF_3CF_2CF_2CH=CFCF_2CF_3$ with HF over a carbon-containing catalyst in accordance with this invention; the gem-dihydropolyfluoroalkane $CF_3CH_2CF_2CF_2CF_2CF_2CF_2CF_3$ can be produced by reacting $CF_3CH=CFCF_2CF_2CF_2CF_2CF_3$ with HF over a carbon-containing catalyst in accordance with this invention; the gem-dihydropolyfluoroalkane $CF_3CF_2CH_2CF_2CF_2CF_2CF_2CF_3$ can be produced by reacting $CF_3CF=CHCF_2CF_2CF_2CF_2CF_3$ and/or $CF_3CF_2CH=CFCF_2CF_2CF_2CF_3$ with HF over a carbon-containing catalyst in accordance with this invention; the gem-dihydropolyfluoroalkane $CF_3CF_2CF_2CH_2CF_2CF_2CF_2CF_3$ can be produced by reacting $CF_3CF_2CF_2CH=CFCF_2CF_2CF_3$ and/or $CF_3CF_2CF=CHCF_2CF_2CF_2CF_3$ with HF over a carbon-containing catalyst in accordance with this invention; the compound

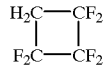

can be produced by reacting

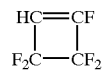

with HF over a carbon-containing catalyst in accordance with this invention; the compound

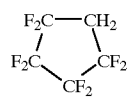

can be produced by reacting

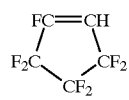

with HF over a carbon-containing catalyst in accordance with this invention; and the compound

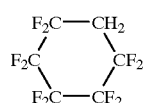

can be provided by reacting

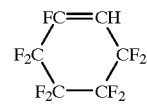

with HF over a carbon-containing catalyst in accordance with this invention.

The reaction temperature for this hydrofluorination reaction should generally be from 200° C. to 500° C. A preferred temperature range is from 300° C. to 450° C. The pressure of the reaction may be within a wide range, from less than 1 atmosphere to extremely high pressures (e.g., 50 atmospheres or more), but normally pressures from 1 atmosphere to about 30 atmospheres are preferred, with higher pressures (e.g., 5 atmospheres or more) favoring the production of saturated products. The reaction time for the hydrofluorination may also be within a wide range depending upon such factors as the materials present and the yield desired. Normally the reaction times between about 15 seconds and 10 hr are suitable.

The amount of hydrogen fluoride provided for contact with the olefinic starting material should represent at least one molecule of hydrogen fluoride for each olefinic bond to be saturated, and is preferably 10 times said minimum, or less (i.e., the molar ratio of hydrogen fluoride available for reacting to olefinic starting material is preferably between 10:1 and 1:1). The hydrogen fluoride can be fed either in the pure state or diluted with an inert gas (e.g., nitrogen, helium or argon).

$CF_3CH=CFCF_3$ can be prepared according to R. D. Chambers and A. J. P. Palmer, Tetrahedron, 25, 4217–24 (1969). 1,3,3,4,4-pentafluorocyclobutene can be prepared according to R. Sullivan et al., J. Org. Chem., 29, 3664–68 (1964). 1,3,3,4,4,5,5-heptafluorocyclopentene can be prepared according to R. E. Banks et al., J. Organomet. Chem., 29, 427–31 (1971). 1,3,3,4,4,5,5,6,6-nonafluorocyclohexane can be prepared according to V. V. Bardin et al., J. Fluor. Chem., 49, 385–400 (1990).

Other olefinic starting materials for this process (e.g., the 5–8 carbon atom monohydrogen-containing olefinic materials of this invention selected from the group consisting of $CF_3CH=CFCF_2CF_3$, $CF_3CF=CHCF_2CF_3$, $CF_3CH=CF(CF_2)_2CF_3$, $CF_3CF_2CH=CFCF_2CF_3$, $CF_3(CF_2)_2CH=CFCF_3$, $CF_3CH=CF(CF_2)_3CF_3$, $CF_3CF_2CH=CF(CF_2)_2CF_3$, $CF_3(CF_2)_2CH=CFCF_2CF_3$, $CF_3(CF_2)_3CH=CFCF_3$, $CF_3CH=CF(CF_2)_4CF_3$, $CF_3CF_2CH=CF(CF_2)_3CF_3$, $CF_3(CF_2)_2CH=CF(CF_2)_2CF_3$, $CF_3(CF_2)_3CH=CFCF_2CF_3$, and $CF_3(CF_2)_4CH=CFCF_3$) may be prepared by hydrogenating a corresponding perfluoroolefin and then dehydrofluorinating the resulting dihydrocompound (i.e., $R^7CF=CFR^8 + H_2 \rightarrow R^7CHFCHFR^8 \rightarrow R^7CH=CFR^8 + R^7CF=CHR^8 + HF$, wherein $R^7$ and $R^8$ are as defined above).

The olefins of the formula $R^7CF=CFR^8$ may be prepared as disclosed in above referenced U.S. patent application Ser. No. 07/595,839. According to the teaching therein, $CF_3CF=CFCF_2CF_3$ may be prepared by reacting perfluoropropene-2 with tetrafluoroethylene (TFE) by the procedure described in Example C below. Perfluoropentene-2 may be converted to 2H,3H-perfluoropentane by reaction of the olefin with hydrogen over a Pd/alumina catalyst as described in Example 8 of above referenced U.S. patent application Ser. No. 07/595,840. 2H,3H-Perfluoropentane may be converted to a mixture of 2H-perfluoropentene-2 and 3H-perfluoropentene-2 by reaction over a carbon catalyst as described in Example 11 below.

Six-carbon monohydroperfluoroolefinic starting materials may be prepared by the following sequence of reactions. Six-carbon perfluoroolefinic starting materials may be prepared by the reaction, substantially, according to the procedure of Example A in U.S. patent application Ser. No. 07/595,840, of 1,1,1,4,4,4-hexafluoro-2,3-dichloro-2-butene with TFE to yield an intermediate product comprising perfluoro-2,3-dichloro-2-hexene. This product then can be converted to a mixture of perfluoro-2-hexene and perfluoro-3-hexene by reaction with potassium fluoride in refluxing N-methylpyrrolidone. Perfluoro-2-hexene and perfluoro-3-hexene can be converted to $CF_3CHFCHFCF_2CF_2CF_3$ and $CF_3CF_2CHFCHFCF_2CF_3$ respectively by reaction of the olefin with hydrogen over a Pd/alumina catalyst as described in Example 8 of U.S. patent application Ser. No. 07/595,840. 2H,3H-Perfluorohexane and 3H,4H-perfluorohexane can be converted to a mixture of $CF_3CH=CF(CF_2)_2CF_3$, $CF_3CF_2CH=CFCF_2CF_3$, and $CF_3(CF_2)_2CH=CFCF_3$ by reaction over a carbon catalyst in a manner analogous to Example 11 below.

Seven-carbon monohydroperfluoroolefinic starting materials may be prepared by the following sequence of reactions. Seven-carbon perfluoroolefinic starting materials may be prepared by the reaction, substantially according to the procedure of Example 3 in U.S. patent application Ser. No. 07/595,839, of perfluoropropene-2 with two moles of tetrafluoroethylene to yield a product comprising perfluoroheptene isomers. Perfluoro-2-heptene and perfluoro-3-heptene can be converted to $CF_3CHFCHF(CF_2)_3CF_3$ and $CF_3CF_2CHFCHF(CF_2)_2CF_3$ respectively by reaction of the olefin with hydrogen over a Pd/alumina catalyst as described in Example 8 of U.S. patent application Ser. No. 07/595,840. 2H,3H-Perfluoroheptane and 3H,4H-perfluoroheptane can be converted to a mixture of $CF_3CH=CF(CF_2)_3CF_3$, $CF_3CF_2CH=CF(CF_2)_2CF_3$, $CF_3(CF_2)_2CH=CFCF_2CF_3$, and $CF_3(CF_2)_3CH=CFCF_3$ by reaction over a carbon catalyst in a manner analogous to Example 11 below.

Eight-carbon monohydroperfluoroolefinic starting materials may be prepared by the following sequence of reactions. Eight-carbon perfluoroolefinic starting materials may be prepared by the reaction, substantially according to the procedure of Example A in U.S. patent application Ser. No. 07/595,839, of 1,1,1,4,4,5,5,6,6,6-decafluoro-2,3-dichloro-2-hexene with TFE to yield an intermediate product comprising perfluoro-4,5-dichloro-4-octene. This product then may be converted to a mixture of perfluoro-2-octene, perfluoro-3-octene, and perfluoro-4-octene by reaction with potassium fluoride in refluxing N-methylpyrrolidone. Perfluoro-2-octene, perfluoro-3-octene, and perfluoro-4-octene can be converted to $CF_3CHFCHF(CF_2)_4CF_3$, $CF_3CF_2CHFCHF(CF_2)_3CF_3$ and $CF_3(CF_2)_2CHFCHF(CF_2)_2CF_3$ respectively by reaction of the olefin with hydrogen over a Pd/alumina catalyst as described in Example 8 of U.S. patent application Ser. No. 07/595,840. 2H,3H-Perfluoro-octane, 3H,4H-perfluoro-octane and 4H,5H-perfluoro-octane can be converted to a mixture of $CF_3CH=CF(CF_2)_4CF_3$, $CF_3CF_2CH=CF(CF_2)_3CF_3$, $CF_3(CF_2)_2CH=CF(CF_2)_2CF_3$, $CF_3(CF_2)_3CH=CFCF_2CF_3$ and $CF_3(CF_2)_4CH=CFCF_3$ by reaction over a carbon catalyst in a manner analogous to Example 11 below.

The gem-dihydropolyfluoroalkanes of this invention are useful as solvents (especially those compounds having boiling points of 100° C. or less) or as refrigerants. They are replacements for currently environmentally suspect chlorofluorocarbons such as trichlorotrifluoroethane. They have zero ozone depletion potential. They are non-flammable. These polyfluoroalkanes may be used by themselves or in combination with other miscible solvents as cleaning agents or defluxing agents for solid surfaces, for example, printed wire boards. The compounds having boiling points above 75° C. are useful as vapor degreasers. The compounds of this invention may also be used as drying agents.

Gem-dihydropolyfluoroalkanes of the formula $R^7CH_2CF_2R^8$ (wherein $R^7$ and $R^8$ are as described above) are miscible with various solvents conventionally used in cleaning operations. Compositions suitable for use in cleaning operations can be prepared which comprise a mixture of gem-dihydropolyfluoroalkanes of the formula $R^7CH_2CF_2R^8$ with one or more compounds selected from the group consisting of alcohols, ethers, esters, ketones, nitromethane, acetonitrile, and halogenated hydrocarbons. Of particular note are cleaning compositions which comprise a mixture of gem-dihydropolyfluoroalkanes of the formula $R^1CH_2CF_2R^2$ (wherein $R^1$ and $R^2$ are as described above) with one or more alcohols, ethers, esters, ketones, nitromethane, acetonitrile and/or halogenated hydrocarbons. The preferred alcohols and halogenated hydrocarbons contain from 1 to 4 carbon atoms; the preferred ethers contain from 2 to 6 carbon atoms; and the preferred esters and ketones contain from 3 to 6 carbon atoms. Examples of suitable alcohols include methanol, ethanol and isopropanol. Examples of suitable ethers include tetrahydrofuran and diethyl ether. Examples of suitable ketones include acetone and methylethylketone. Examples of suitable halogenated hydrocarbons include methylene chloride (i.e., dichloromethane), 1,1,2-trichloro-1,2,2-trifluoroethane, trichloroethene, 1,1-dichloroethane, and cis- and trans-1,2-dichloroethylene. Preferably, such compositions contain at least about 5 percent by weight total of the gem-dihydropolyfluoro-alkanes of the formula $R^7CH_2CF_2R^8$ and/or the formula $R^1CH_2CF_2R^2$; and can contain up to 99 percent by weight, or even more thereof. Preferred compositions include mixtures of one or more of $CF_3CH_2CF_2CF_2CF_3$, $CF_3CF_2CH_2CF_2CF_3$, $CF_3CH_2CF_2CF_2CF_2CH_3$, and $CF_3CF_2CH_2CF_2CF_2CF_3$ with one or more of said alcohols, ethers, esters, ketones, nitromethane, acetonitrile and halogenated hydrocarbons. Most preferred with respect to ozone depletion potential are compositions in which no component contains chlorine.

The mixtures of this invention are useful in a wide variety of processes for cleaning solid surfaces which comprise treating said surface therewith. Applications include removal of flux and flux residues from printed circuit boards contaminated therewith.

Compositions which comprise an admixture of effective amounts of one or more gem-dihydropolyfluoroalkanes of the formula $R^7CH_2CF_2R^8$ and/or the formula $R^1CH_2CF_2R^2$ with one or more solvents selected from the group consisting of alcohols, ethers, esters, ketones, nitromethane, acetonitrile and halogenated hydrocarbons to form an azeotrope or azeotrope-like mixture are considered especially useful. Compositions which are mixtures of $CF_3CH_2CF_2CF_2CF_3$ and/or $CF_3CF_2CH_2CF_2CF_3$ with alcohol selected from the group consisting of methanol, ethanol and isopropanol are preferred.

By azeotrope or azeotrope-like is meant constant boiling liquid admixtures of two or more substances which admixtures behave like a single substance in that the vapor produced by partial evaporation or distillation has the same composition as the liquid, i.e., the admixtures distill without a substantial change in composition. Constant boiling compositions characterized as azeotropes or azeotrope-like exhibit either a maximum or minimum boiling point as compared with that of nonazeotropic mixtures of the same substances.

By effective amounts is meant the amounts of each component of the admixture of the instant invention, which, when combined, results in the formation of the azeotrope or azeotrope-like admixture of the instant invention.

It is possible to fingerprint, in effect, a constant boiling admixture, which may appear under varying guises depending on the conditions chosen, by any of several criteria.

The composition may be defined as an azeotrope of its components, say component A and component B, since the very term "azeotrope" is at once both definitive and limitive, requiring that effective amounts of A and B form this unique composition of matter which is a constant boiling admixture. It is well known by those who are skilled in the art that at differing pressures, the composition of a given azeotrope will vary, at least to some degree, and changes in distillation pressures also change, at least to some degree, the distillation temperatures. Thus, an azeotrope of A and B represents a unique type of relationship but with a variable composition depending on temperature and/or pressure. Therefore, compositional ranges, rather than fixed compositions, are often used to define azeotropes.

Or, the composition can be defined as a particular weight relationship or mole percent relationship of A and B, while recognizing that such specific values point out only one particular such relationship and that in actuality a series of such relationships represented by A and B actually exist for a given azeotrope, varied by influence of distillative conditions of temperature and pressure.

Or, recognizing that the azeotrope A and B does represent just such a series of relationships, the azeotropic series represented by A and B can be characterized by defining the composition as an azeotrope characterized by a boiling point at a given pressure, thus giving identifying characteristics without unduly limiting the scope of the invention by a specific numerical composition, which is limited by and is only as accurate as the analytical equipment available.

Azeotrope or azeotrope-like compositions are provided in accordance with this invention which comprise admixtures of effective amounts of a gem-dihydropolyfluoroalkane (e.g., $CF_3CH_2CF_2CF_2CF_3$) with an alcohol selected from the group consisting of methanol, ethanol and isopropanol to form an azeotrope or azeotrope-like mixture.

In accordance with this invention, compositions which are two-component mixtures of (i) from about 91 to 99 weight percent total of at least one of $CF_3CH_2CF_2CF_2CF_3$ and $CF_3CF_2CH_2CF_2CF_3$, and (ii) from about 1 to 9 weight percent methanol are characterized as azeotropes or azeotrope-like in that mixtures within this range exhibit a substantially constant boiling point. Being substantially constant boiling, the mixtures do not tend to fractionate to any great extent upon evaporation. After evaporation, only a small difference exists between the composition of the vapor and the composition of the initial liquid phase. This difference is so small that the compositions of the vapor and liquid phases are considered substantially identical. Accordingly, any mixture within this range exhibit properties which are characteristic of a true binary azeotrope. The binary composition consisting essentially of about 95 weight percent $CF_3CH_2CF_2CF_2CF_3$ and about 5 weight percent methanol has been established, within the accuracy of the fractional distillation method, as a true binary azeotrope, boiling at about 40° C. at substantially atmospheric pressure and is a preferred azeotrope of this invention.

Also, in accordance with this invention, compositions which are two-component mixtures of (i) from about 93 to 99 weight percent total of at least one of $CF_3CH_2CF_2CF_2CF_3$ and $CF_3CF_2CH_2CF_2CF_3$, and (ii) from about 1 to 7 weight percent ethanol are characterized as an azeotrope or azeotrope-like in that mixtures within this range exhibit a substantially constant boiling point. Being substantially constant boiling, the mixtures do not tend to fractionate to any great extend upon evaporation. After evaporation, only a small difference exists between the composition of the vapor and the composition of the initial liquid phase. This difference is so small that the compositions of the vapor and liquid phases are considered substantially identical. Accordingly, any mixture within this range exhibits properties which are characteristic of a true binary azeotrope. The binary composition consisting essentially of about 97 weight percent $CF_3CH_2CF_2CF_2CF_3$ and about 3 weight percent ethanol has been established, within the accuracy of the fractional distillation method, as a true binary azeotrope, boiling at about 45° C. at substantially atmospheric pressure and is a preferred azeotrope of this invention.

Also, in accordance with this invention, compositions which are two-component mixtures of (i) from about 93 to 99 weight percent total of at least one of $CF_3CH_2CF_2CF_2CF_3$ and $CF_3CF_2CH_2CF_2CF_3$, and (ii) from about 1 to 7 weight percent isopropanol are characterized as an azeotrope or azeotrope-like in that mixtures within this range exhibit a substantially constant boiling point. Being substantially constant boiling, the mixtures do not tend to fractionate to any great extent upon evaporation. After evaporation, only a small difference exists between the composition of the initial liquid phase. This difference is so small that the compositions of the vapor and liquid phases are considered substantially identical. Accordingly, any mixture within this range exhibits properties which are characteristic of a true binary azeotrope. The binary composition consisting essentially of about 97 weight percent $CF_3CH_2CF_2CF_2CF_3$ and about 3 weight percent isopropanol has been established, within the accuracy of the fractional distillation method, as a true binary azeotrope, boiling at about 46° C. at substantially atmospheric pressure, and is a preferred azeotrope of this invention.

The compositions of the invention may be used in conventional apparatus, employing conventional operating techniques, The solvent(s) may be used without heat if desired, but the cleaning action of the solvent may be assisted by conventional means (e.g., heating, agitation, etc.). In some applications (e.g., removing certain tenacious fluxes from soldered components) it may be advantageous to use ultrasonic irradiation in combination with the solvent(s).

Compositions provided in accordance with this invention can be used in cleaning processes such as us described in U.S. Pat. No. 3,881,949 and U.S. Pat. No. 4,715,900, both of which are incorporated herein by reference.

The mixtures of the instant invention can be prepared by any convenient method including mixing or combining the desired amounts of the components. A preferred method is to weigh the desired amounts of each component and thereafter combine them in an appropriate container.

Practice of the invention will become further apparent from the following non-limiting examples.

EXAMPLES

Example A

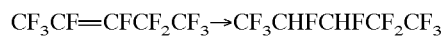

Palladium/Alumina

A 6"×½" O.D. Hastelloy™ nickel alloy tube reactor was charged with 0.5% Pd/alumina (10.0 g, 5×8 mesh spheres).

This catalyst was reduced with hydrogen prior to use. Vaporized perfluoropentene-2 (2 mL/hr) and hydrogen (20 cc/min) were co-fed to the reactor. The reaction products were analyzed by on-line GC and on-line MS and the products were collected in a −80° C. trap. At temperatures of 100–200° C., conversions were 96–99% and ≧95% yields of perfluoro-2H,3H-pentane were obtained. The major by-products were about 1% of the trihydroperfluoropentanes. Pure dihydro-product, bp 50–55° C. was obtained by a simple fractionation and was shown by GC and NMR analyses to have a ratio of diastereomers of about 9:1.

Example B

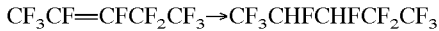

Hydrogen/Iodine

A metal rocker tube charged with iodine (97.4 g, 0.384 mol) and perfluoropentene-2 (191.8 g, 0.767 mol) was cooled, evacuated, pressured with hydrogen (100 psi), and heated to 300° C. The hydrogen pressure was raised to and maintained at 1000 psi and 300° C. for one day. The rocker tube was cooled to 5° C. gases vented, and the cold product (157.2 g, 99% pure by GC) was washed with cold aqueous $Na_2S_2O_3$, dried over $Na_2SO_4$, to yield decafluoro-2H,3H-pentane, bp 43–52° C., as two diastereomers in a 49:51 ratio.

Example C

Preparation of $CF_3CF=CFCF_2CF_3$

A 400 mL metal tube charged at −20° C. with $AlF_{2.8}Cl_{0.2}$ (8.0 g), prepared from $AlCl_3$ and $CCl_3F$, hexafluoropropene (75.0 g, 0.50 mol), and tetrafluoroethylene (50 g, 0.50 mol) was shaken for 30 min. During this time the temperature rose quickly to 20° C. and the pressure dropped to 8 psi. Distillation of the product afforded perfluoropentene-2 (88.0 g, 70% yield), bp 23–26° C., identified by IR, NMR and GC/MS. NMR showed the product to contain 89% of the trans-isomer and 11% of the cis-isomer.

Example D

Preparation of $CF_3CH=CFCF_2CF_3$

A 400 mL metal tube charged at −20° C. with $AlF_{2.8}Cl_{0.2}$ (6.0 g), prepared from $AlCl_3$ and $CCl_3F$, 2H-pentafluoropropene (66.0 g, 0.50 mol), and tetrafluoroethylene (50 g, 0.50 mol) was shaken for 3.5 hr. During this time the temperature rose quickly to 25° C. and the pressure dropped to 0 psi from an initial pressure of 153 psi. Distillation of the product afforded 80% 2H-perfluoropentene-2 identified by IR, NMR and GC/MS.

Example 1

Addition to HF to Nonafluoro-2H-pentene-2 to Form Decafluoro-2H,2H-pentene (HFC-43-10mf)

A 200mL Hastelloy® nickel alloy tube charged with PCB carbon (25 g, previously dried under vacuum at 300–350° C.), nonafluoro-2H-pentene-2 (23.2 g, 0.10 mol), and HF (10 g, 0.5 mol) was heated at 300° C. for 4 hr under autogenous pressure. The tube was cooled, and the recovered dry black solid was stirred with a solution of calcium chloride (20 g) in water (100 mL), then distilled to give a two-phase distillate. The lower layer (15 g), was indicated by GC/MS to consist of 54.6% of starting olefin and 45.1% of decafluoro-2H,2H-pentane, with minor amounts of two impurities.

The distilled dihydro-product ca. 98% pure, bp 46–47° C. was characterized by $^1H$ and $^{19}F$ NMR and the structure was confirmed as decafluoro-2H,2H-pentane, IR (neat): 3029 and 2987 (sat'd CH), 1300–1150 $cm^{-1}$ (CF).

Example 2

Addition of HF to Nonafluoro-2H-pentene-2 to Form Decafluoro-2H,2H-pentane (HFC-43-10mf)

A 200-mL Hastelloy® nickel alloy tube charged with PCB carbon (25 g, previously dried under vacuum at 300–350° C.), nonafluoro-2H-pentene-2 (23.3 g, 0.10 mol), and HF (10 g, 0.5 mol) was heated at 300° C. for 12 hr under autogenous pressure. The tube was cooled, and the recovered dry black solid was stirred with a solution of calcium chloride (20.8 g) in water (100 mL), then distilled to give a two-phase distillate. Analysis of the crude volatile product showed it to contain 13% of starting olefin and 87% of decafluoro-2H,2H-pentane.

Example 3

Addition of HF to Nonafluoro-2H-pentene-2 to Form Decafluoro-2H,2H-pentane (HFC-43-10mf)

A 1.4 L Hastelloy® nickel alloy tube charged with PCB carbon (175 g, previously dried in a stream of nitrogen at 150° C.), nonafluoro-2H-pentene-2 (170 g, 0.73 mol), and HF (70 g, 3.5 mol) was heated at 300° C. for 16 hr under autogenous pressure. The tube was cooled, and the recovered dry black solid was stirred with a solution of calcium chloride (210 g) in water (800 mL), then distilled to give a two-phase distillate. The lower layer (100.5 g) gave 25% isolated yield (46.9 g) of decafluoro-2H,2H-pentane, bp 47° C.

Example 4

Addition of HF to Heptafluoro-1H-cyclopentene to Form Octafluoro-1H,1H-cyclopentane

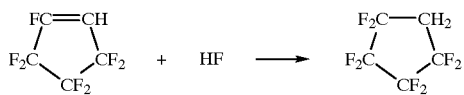

Heptafluoro-1H-cyclopentene was prepared as described in U.S. Pat. No. 3,449,304 (col. 1, line 47 through col. 2, line 39). A mixture of dried PCB carbon (25 g) heptafluoro-1H-cyclopentene (24 g, 0.12 mol) and HF (10 g, 0.5 mol) was heated in a 200-mL Hastelloy® nickel alloy tube at 300° C. for 12 hr. The product was contact with aq. $CaCl_2$ and distilled in the usual way to give 5.0 g of liquid, indicated by GC/MS to contain 59.1% of starting cycloolefin and 40.3% of product $C_5H_2F_8$. NMR showed the 40.3% component to be octafluoro-1H,1H-cyclopentane.

Example 5

Rearrangement of Decafluoro-2H,3H-pentane to Decafluoro-2H,2H-pentane and Decafluoro-3H,3H-pentane

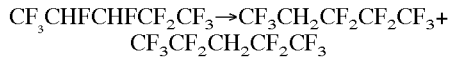

A mixture of decafluoro-2H,3H-pentane (25.4 g, 0.10 mol), prepared as described above in Example B, dried PCB carbon (25 g), and HF (10 g, 0.5 mol) was heated in a 200mL Hastelloy® nickel alloy tube at 300° C. for 12 hr.

Work-up of the reaction mixture in the usual way by contacting with aq. $CaCl_2$ and distillation afforded 12.3 of liquid. Analysis by GC/MS and $^1H$ and $^{19}F$ NMR showed it to contain 25% of decafluoro-2H,2H-pentane, 18.5% of decafluoro-3H,3H-pentane, 15% of nonafluoro-2H-pentene-2, and 4% of nonafluoro-3H-pentene-2, along with 36.5% of recovered 2H,3H starting material.

Example 6

Rearrangement of Decafluoro-2H,3H-pentane to Decafluoro-2H,2H-pentane and Decafluoro-3H,3H-pentane

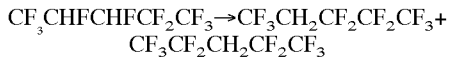

A mixture of decafluoro-2H,3H-pentane (25.2 g, 0.10 mol), prepared as described above in Example B, dried 2% $CrCl_3$ on PCB carbon (20 g), and HF (10 g, 0.5 mol) was heated in a 200 mL Hastelloy® nickel alloy tube at 300° C. for 12 hr.

Work-up of the reaction mixture in the usual way by contacting with aq. $CaCl_2$ and distillation afforded 13.0 g of liquid. Analysis by GC/MS and $^1H$ and $^{19}F$ NMR showed it to contain 4.1% of decafluoro-2H,2H-pentane, 4.1% of decafluoro-3H,3H-pentane, 8.2% of nonafluoro-2H-pentene-2, and 3.1% of nonafluoro-3H-pentene-2, along with 80.6% of recovered 2H,3H starting material.

Example 7

Rearrangement of Decafluoro-2H,3H-pentane to Decafluoro-2H,2H-pentane and Decafluoro-3H,3H-pentane

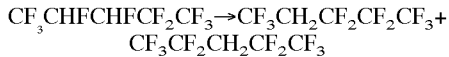

A mixture of decafluoro-2H,3H-pentane (25.2 g, 0.10 mol), prepared as described above in Example B, dried 2% Darco™ activated carbon (23 g, 4×12 mesh), and HF (10 g, 0.5 mol) was heated in a 200 mL Hastelloy® nickel alloy tube at 300° C. for 12 hr.

Work-up of the reaction mixture in the usual way by contacting with aq. $CaCl_2$ and distillation afforded 14.0 of liquid. Analysis by GC/MS and $^1H$ and $^{19}F$ NMR showed it to contain 3.8% of decafluoro-2H,2H-pentane, 4.1% of decafluoro-3H,3H-pentane, 14.0% of nonafluoro-2H-pentene-2, and 5.1% of nonafluoro-3H-pentene-2, 3.2% nonafluoro-2H,2H,3H-pentane, 1.3% nonafluoro-2H,3H,3H-pentane, along with 67.3% of recovered 2H,3H starting material.

Example 8

Rearrangement of Decafluoro-2H,3H-pentane to Decafluoro-2H,2H-pentane and Decafluoro-3H,3H-pentane

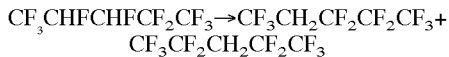

A mixture of decafluoro-2H,3H-pentane (25 g, 0.10 mol), prepared as described above in Example B, dried PCB carbon of the type listed as NAW in Table 1 below (25 g, 12×30 mesh), and HF (10 g, 0.5 mol) was heated in a 200 mL Hastelloy™ nickel alloy tube at 300° C. for 12 hr.

Work-up of the reaction mixture in the usual way by contacting with aq. $CaCl_2$ and distillation afforded 11.1 g of liquid. Analysis by GC/MS and $^1H$ and $^{19}F$ NMR showed it to contain 5.6% of decafluoro-2H,2H-pentane, 5.6% of decafluoro-3H,3H-pentane, 8.8% of nonafluoro-2H-pentene-2, and 2.5% of nonafluoro-3H-pentene-2, along with 77.5% of recovered 2H,3H starting material.

Example 9

Rearrangement of Decafluoro-2H,3H-pentane to Decafluoro-2H,2H-pentane and Decafluoro-3H,3H-pentane

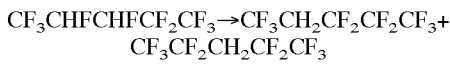

A mixture of decafluoro-2H,3H-pentane (25 g, 0.10 mol), prepared as described above in Example B, dried HCl-washed (traces only of K+ left) PCB carbon (10.4 g, 12×30 mesh), and HF (10 g, 0.5 mol) was heated in a 200 mL Hastelloy® nickel alloy tube at 300° C. for 12 hr.

Work-up of the reaction mixture in the usual way by contacting with aq. $CaCl_2$ and distillation afforded 11.0 g of liquid. Analysis by GC/MS and $^1H$ and $^{19}F$ NMR showed it to contain 2.1% of decafluoro-2H,2H-pentane, 2.1% of decafluoro-3H,3H-pentane, 5.2% of nonafluoro-2H-pentene-2, and 2.1% of nonafluoro-3H-pentene-2, along with 88.7% of recovered 2H,3H starting material.

Comparative Example

Rearrangement of Decafluoro-2H,3H-pentane to Decafluoro-2H,2H-pentane and Decafluoro-3H,3H-pentane

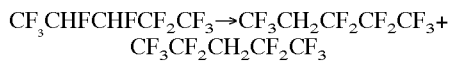

A mixture of decafluoro-2H,3H-pentane (25 g, 0.10 mol as a mixture of two disastereomers in 96:4 ratio), prepared by the hydrogenation of perfluoropentene-2 over a 5% Pd on carbon catalyst; and HF (10 g, 0.5 mol) was heated in a 200 mL Hastelloy® nickel alloy tube at 300° C. for 12 hr.

Work-up of the reaction mixture in the usual way by contacting with aq. $CaCl_2$ and distillation afforded 9.9 g of liquid. Analysis by GC/MS and $^1H$ and $^{19}F$ NMR showed it to contain only recovered 2H,3H starting material.

Example 10

Rearrangement of Octafluoro-2H,3H-butane to Octafluoro-2H,2H-butane

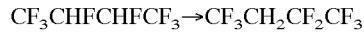

Reaction of octafluoro-2H,3H-butane (20 g, 0.099 mol) with of PCB carbon (25 g) and HF (10 g, 0.50 mol) for 12 hr at 300° C. gave, after contacting with aq. $CaCl_2$, 8.3 g of volatiles. Analysis by GC/MS and NMR showed 3.4% of octafluoro-2H,2H-butane and 2.1% of heptafluoro-2H-butene-2 to be present as products.

General Procedure for Examples 11–15

The reactor (0.5 inch ID×12 inch Inconel® nickel alloy pipe) was charged with a catalyst and placed in a sand bath. The bath was gradually heated to 400° C. while nitrogen gas at a flow rate of 50 cc/min. was passed through the reactor to remove traces of water. After the water was removed, the temperature of the bath was adjusted to the indicated value and HF and 1,1,1,2,3,4,4,5,5,5-decafluoropentane (HFC-43-10mee) were fed to the reactor. The HFC-43-10mee was a 99% pure mixture of diastereomers containing small amounts of the following impurities; $CF_3CHFCHF_2$, $CF_3CF=CFC_2F_5$, and unknowns.

The reactor effluent was sampled on-line with a Hewlett Packard HP 5890 gas chromatography using a 20 ft. long, 1/8" diameter, column containing Krytox® perfluorinated polyether on an inert support and a helium flow of 35 cc/min. Gas chromatographic conditions were 70° C. for 3 min. followed by temperature programming to 180° C. at a rate of 6° C./min. Product analyses are reported as relative area %.

Example E

Preparation of HCl-Washed Carbon

A commercially available carbon (500 g, 6×16 mesh granules) was soaked for 120 hr with gentle stirring in 1M HCl. The carbon granules were collected on a fritted glass funnel and washed with deionized water until the washings were chloride free. Finally the carbon granules were dried at 120° C. for 60 hr followed by calcination at 300° C. in air to obtain 468.8 g of dried, calcined granules. The ash content and the elements present in the ash are shown in Table 1.

Example F

Preparation of HCl/HF-Washed Carbon

HCl-washed carbon (225 g, 6×16 mesh granules) prepared as described above was soaked in for 48 hr at room temperature with occasional stirring in 1M HF (3 L) in an HF-resistant container. The carbon granules were then placed in a 4 L HF-resistant container on a steam bath and washed with deionized water (3 L portions, at about 50° C.) until the washings had a pH greater than 4.0. Finally the carbon granules were dried at 150° C. for 60 hr in air followed by calcination at 300° C. in air for 3 hr to obtain 216.6 g of dried calcined granules. The ash content and the elements present in the ash are shown in Table 1.

Example G

Preparation of $CrCl_3$ On HCl-Washed Carbon $CrCl_3.6H_2O$ (4.04 g) was dissolved in deionized water (56 mL) and the entire solution poured over 40 g of HCl-washed carbon granules (6×16 mesh). The resulting mixture was allowed to stand at room temperature for 1 hr and then placed in a convection oven at 120° C. for 16 to 24 hr to remove the water. It was then pretreated by heating in an atmosphere of nitrogen gas at 450° C. followed by heating in HF at 450° C. prior to its use as a catalyst.

TABLE 1

Elemental Analysis of Carbon Granules

| | C1W[a] (ppm) | C1FW[b] (ppm) | NAW[c] (ppm) |
|---|---|---|---|
| P | | | 330 |
| S | | | 380 |
| Si | 760 | 74 | 900 |
| Cu | 18 | 3 | 21 |
| Mn | 1 | <1 | 15 |
| Fe | 65 | 25 | 205 |
| Ba | <1 | | 12 |

TABLE 1-continued

Elemental Analysis of Carbon Granules

| | C1W[a] (ppm) | C1FW[b] (ppm) | NAW[c] (ppm) |
|---|---|---|---|
| Ca | 17 | | 650 |
| Zn | <3 | <1 | <5 |
| Mg | 21 | | |
| K | 28 | | 9500 |
| Al | <240 | | 290 |
| Na | 250 | | 730 |
| Ti | <30 | 12 | 10 |
| Ash | 0.18% | 0.01% | 2.18% |

[a]C1W = HCl-washed carbon
[b]C1FW = HCl/HF-washed carbon
[c]NAW = non-acid washed carbon

Example 11

Dehydrofluorination of Decafluoro-2H,3H-pentane

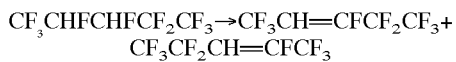

The General Procedure described above was followed. The catalyst was a commercial PCB carbon (15.6 g, 30 mL, 12×30 mesh). HF and HFC-43-10mee in a molar ratio of 2:1 and with a contact time of 60 sec. at atmospheric pressure were fed to the reactor. The results of experiments at different temperatures are shown in Table 2.

TABLE 2

| Time hr. | Temp. ° C. | 43-10mee (a) % Conv | F1429 (b) % Sel. | F1438 (c) % Sel. | 43-10mcf (d) % Sel. | 43-10mf (e) % Sel. |
|---|---|---|---|---|---|---|
| 1 | 400 | 100 | 93.0 | 2.4 | 0.5 | 0.5 |
| 2 | 400 | 100 | 94.1 | 0.5 | 0.5 | 0.5 |
| 3 | 400 | 100 | 94.1 | 0.3 | 0.5 | 0.5 |
| 4 | 400 | 100 | 93.7 | 0.2 | 0.5 | 0.6 |
| 5 | 350 | 100 | 94.1 | <0.1 | 1.4 | 1.8 |
| 6 | 325 | 100 | 91.3 | 0.2 | 2.2 | 3.9 |
| 7 | 300 | 98.8 | 86.0 | 0.1 | 3.5 | 8.0 |
| 8 | 275 | 82.7 | 80.2 | <0.1 | 6.0 | 11.7 |
| 9 | 250 | 43.8 | 77.3 | 0.2 | 9.2 | 10.4 |
| 10 | 225 | 9.6 | 80.8 | 0.2 | 6.3 | 5.0 |

(a) 43-10mee is a 99% pure mixture of $CF_3CHFCHFCF_2CF_3$ diastereomers.
(b) F1429 is a mixture of cis and trans isomers of $CF_3CH=CFCF_2CF_3$ and $CF_3CF_2CH=CFCF_3$ and trace amounts of other olefins.
(c) F1438 is an olefin of the formula $C_5H_2F_8$.
(d) 43-10mcf is $CF_3CF_2CH_2CF_2CF_3$.
(e) 43-10mf is $CF_3CH_2CF_2CF_2CF_3$.

Example 12

Dehydrofluorination of Decafluoro-2H,3H-pentane

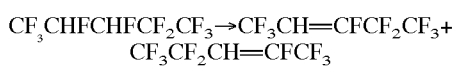

The General Procedure described above was followed. The catalyst was a commercial carbon that had been washed with hydrochloric and hydrofluoric acid (13.4 g, 30 mL, 6×16 mesh). HF and HFC-43-10mee in a molar ratio of 2:1, 4:1, or 6:1 and with a contact time of 60 sec. were fed to the reactor. The results of experiments at different temperatures are shown in Table 3.

TABLE 3

| Time hr. | Temp. °C. | molar ratio[a] | 43-10mee (b) % Conv | F1429 (c) % Sel. | 43-10mcf (d) % Sel. | 43-10mf (e) % Sel. |
|---|---|---|---|---|---|---|
| 1 | 200 | 2:1 | 0.9 | 99.9 | — | — |
| 3 | 225 | 4:1 | 8.3 | 94.5 | 4.2 | 1.3 |
| 4 | 250 | 4:1 | 31.2 | 90.5 | 6.7 | 2.8 |
| 7 | 250 | 2:1 | 12.5 | 94.7 | 3.1 | 2.2 |
| 11 | 275 | 2:1 | 36.4 | 93.1 | 3.9 | 3.0 |
| 25 | 275 | 4:1 | 54.0 | 89.2 | 5.8 | 5.0 |
| 31 | 275 | 6:1 | 57.0 | 88.1 | 6.2 | 5.6 |
| 36 | 300 | 2:1 | 73.0 | 92.6 | 3.4 | 4.0 |
| 48 | 300 | 4:1 | 92.4 | 89.0 | 4.0 | 7.1 |
| 56 | 300 | 6:1 | 93.2 | 88.3 | 4.1 | 7.6 |
| 59 | 325 | 2:1 | 99.1 | 93.8 | 2.1 | 4.1 |
| 61 | 325 | 4:1 | 99.8 | 93.1 | 2.4 | 4.4 |
| 63 | 350 | 2:1 | 100 | 96.8 | 1.2 | 2.0 |
| 64 | 350 | 0:1 | 100 | 97.7 | 0.9 | 1.3 |

[a] molar ratio of HF:43-10mee.
(b) 43-10mee is a 99% pure mixture of $CF_3CHFCHFCF_2CF_3$ diastereomers.
(c) F1429 is a mixture of cis and trans isomers of $CF_3CH=CFCF_2CF_3$ and $CF_3CF_2CH=CFCF_3$ and trace amounts of other olefins.
(d) 43-10mcf is $CF_3CF_2CH_2CF_2CF_3$.
(e) 43-10mf is $CF_3CH_2CF_2CF_2CF_3$.

Example 13

Dehydrofluoroination of Decafluoro-2H,3H-pentane

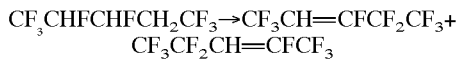

$CF_3CHFCHFCH_2CF_3 \rightarrow CF_3CH=CFCF_2CF_3 + CF_3CF_2CH=CFCF_3$

The General Procedure described above was followed. The catalyst was 6% $CrCl_3$/acid-washed carbon (14.7 g, 30 mL) prepared as described in Example C. HF and HFC-43-10mee in a molar ratio of 2:1 or 4:1, and with a contact time of 60 sec. were fed to the reactor. The results of experiments at different temperatures are shown in Table 4.

TABLE 4

| Time hr. | Temp. °C. | molar ratio[a] | 43-10mee (b) % Conv | F1429 (c) % Sel. | 43-10mcf (d) % Sel. | 43-10mf (e) % Sel. |
|---|---|---|---|---|---|---|
| 1 | 200 | 2:1 | 0.9 | 99.9 | — | — |
| 3 | 225 | 2:1 | 5.8 | 94.4 | 3.7 | 1.9 |
| 4 | 225 | 4:1 | 5.3 | 97.2 | 1.9 | 0.9 |
| 5 | 250 | 4:1 | 19.9 | 93.2 | 4.4 | 2.4 |
| 6 | 275 | 4:1 | 40.2 | 91.7 | 4.5 | 3.8 |
| 7 | 300 | 4:1 | 73.1 | 91.8 | 3.2 | 4.5 |
| 8 | 325 | 4:1 | 99.7 | 91.7 | 2.4 | 4.5 |
| 9 | 350 | 4:1 | 99.9 | 94.2 | 1.5 | 2.1 |
| 10 | 375 | 4:1 | 99.9 | 94.1 | 1.0 | 1.0 |

[a] molar ratio of HF:43-10mee.
(b) 43-10mee is a 99% pure mixture of $CF_3CHFCHFCF_2CF_3$ diastereomers.
(c) F1429 is a mixture of cis and trans isomers of $CF_3CH=CFCF_2CF_3$ and $CF_3CF_2CH=CFCF_3$ and trace amounts of other olefins.
(d) 43-10mcf is $CF_3CF_2CH_2CF_2CF_3$.
(e) 43-10mf is $CF_3CH_2CF_2CF_2CF_3$.

Example 14

Dehydrofluoroination and Rearrangement of Decafluoro-2H,3H-pentane

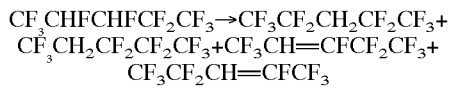

$CF_3CHFCHFCF_2CF_3 \rightarrow CF_3CF_2CH_2CF_2CF_3 + CF_3CH_2CF_2CF_2CF_3 + CF_3CH=CFCF_2CF_3 + CF_3CF_2CH=CFCF_3$ The General Procedure described above was followed. The reactor was a ¾" OD×6" length Inconel® nickel alloy pipe. The catalyst was a carbon that had been washed with hydrochloric and hydrofluoric acid (13.2 g, 30 mL, 6×16 mesh). HF and HFC-43-10mee in a molar ratio of 4:1 were fed to the reactor at 300° C. The results of experiments at different pressures, 100 psi and 200 psi, are shown in Table 5. The conversion of HFC-43-10mee was complete in both cases.

TABLE 5

| Press. psi | F1429[a] % Sel. | 43-10mcf[b] % Sel. | 43-10mf[c] % Sel. |
|---|---|---|---|
| 100 | 43.9 | 16.6 | 32.7 |
| 200 | 34.4 | 20.8 | 40.6 |

[a] F1429 is a mixture of cis and trans isomers of $CF_3CH=CFCF_2CF_3$ and $CF_3CF_2CH=CFCF_3$ and trace amounts of other olefins.
[b] 43-10mcf is $CF_3CF_2CH_2CF_2CF_3$.
[c] 43-10mf is $CF_3CH_2CF_2CF_2CF_3$.

Example 15

Dehydrofluoroination and Rearrangement of Decafluoro-2H,3H-pentane

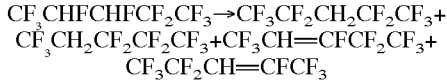

$CF_3CHFCHFCF_2CF_3 \rightarrow CF_3CF_2CH_2CF_2CF_3 + CF_3CH_2CF_2CF_2CF_3 + CF_3CH=CFCF_2CF_3 + CF_3CF_2CH=CFCF_3$ The General Procedure described above was followed. The reactor was a ¾" OD×6" length Inconel® nickel alloy pipe. The catalyst was a carbon that had been washed with hydrochloric and hydrofluoric acid (13.2 g, 30 mL, 6×16 mesh). HFC-43-10mee (3.6 mL/hr) was fed to the reactor at 300° C. and at 200 psi. The results are shown in Table 6. The conversion of HFC-43-10mee was 100% complete.

TABLE 6

| F1429 % Sel. | 43-10mcf % Sel. | 43-10mf % Sel. |
|---|---|---|
| 52.6 | 15.4 | 30.3 |

Example 16

HFC-43-10mf/Methanol

HFC-43-10mf (18.1 g) and methanol (1.0 g) were combined and the mixture was distilled using a spinning band column. The boiling point and composition were monitored for azeotrope formation. A constant boiling azeotrope was formed which had a boiling point of about 40.4° C. Gas chromatographic analysis showed that the azeotrope consisted of 94.4% HFC-43-10mf and 5.1% methanol.

Example 17

HFC-43-10mf/Ethanol

HFC-43-10mf (17.5 g) and absolute ethanol (1.0 g) were combined and the mixture was distilled using a spinning band column. The boiling point and composition were monitored for azeotrope formation. A constant boiling azeotrope was formed which had a boiling point of about 44.6° C. Gas chromatographic analysis showed that the azeotrope consisted of 96.7% HFC-43-10mf and 3.3% ethanol.

Example 18

HFC-43-10mf/Isopropanol

HFC-43-10mf (12.0 g) and isopropanol (1.0 g) combined and the mixture was distilled using a spinning band column. The boiling point and composition were monitored for azeotrope formation. A constant boiling azeotrope was formed which had a boiling point of about 46.0° C. Gas chromatographic analysis showed that the azeotrope consisted of 97.0% HFC-43-10mf and 3.0% isopropanol.

Example 19

Surface Cleaning with HFC-43-10mf/Methanol Azeotrope

A single-sided circuit board is coated with activated rosin flux, and soldered by passing the board over a preheater to obtain a top side board temperature of approximately 200° F. and then through 500° F. molten solder. The soldered board is defluxed in an azeotropic mixture of 94.9 weight percent HFC-43-10mf and 5.1 weight percent methanol by suspending it, first for 3 min. in the boiling sump, then 1 min. in the rinse sump and, thereafter, for 1 min. in the solvent vapor above the boiling sump. The board thus cleaned has no visible residue remaining on it.

Particular embodiments of the invention are included in the Examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A compound having the formula $R^1CH_2CF_2R^2$ wherein $R^1$ is selected from the group consisting of $-CF_2CF_3$ and $-CF_2CF_2CF_3$ and $R^2$ is selected from the group consisting of $-CF_3$, $-CF_2CF_3$ and $-CF_2CF_2CF_3$ or wherein $R^1$ and $R^2$ together are $-(CF_2)_3-$.

2. The compound of claim 1 which is $CF_3CF_2CH_2CF_2CF_2CF_2CF_3$.

3. The compound of claim 1 which is $CF_3CF_2CF_2CH_2CF_2CF_2CF_3$.

4. The compound of claim 1 which is $CF_3CF_2CF_2CH_2CF_2CF_2CF_3$.

5. The compound of claim 1 which is $CF_3CF_2CH_2CF_2CF_2CF_2$.

6. The compound of claim 1 which is $CF_3CF_2CH_2CF_2CF_2CF_3$.

7. The compound of claim 1 which is $CF_3CF_2CH_2CF_2CF_3$.

8. The compound of claim 1 which is

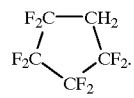

* * * * *